United States Patent
Senoo et al.

(10) Patent No.: US 8,404,914 B2
(45) Date of Patent: Mar. 26, 2013

(54) PROCESS FOR PRODUCING ALKYLATED AROMATIC COMPOUNDS AND PROCESS FOR PRODUCING PHENOL

(75) Inventors: Shinji Senoo, Takaishi (JP); Kazuhiko Kato, Yokohama (JP); Kenji Doi, Ichihara (JP); Katsunari Higashi, Ichihara (JP)

(73) Assignee: Mitsui Chemicals, Inc., Tokyo (JP)

( * ) Notice: Subject to any disclaimer, the term of this patent is extended or adjusted under 35 U.S.C. 154(b) by 260 days.

(21) Appl. No.: 12/997,449

(22) PCT Filed: Jun. 3, 2009

(86) PCT No.: PCT/JP2009/060137
§ 371 (c)(1),
(2), (4) Date: Dec. 10, 2010

(87) PCT Pub. No.: WO2009/150974
PCT Pub. Date: Dec. 17, 2009

(65) Prior Publication Data
US 2011/0087053 A1    Apr. 14, 2011

(30) Foreign Application Priority Data
Jun. 10, 2008 (JP) ................. 2008-151480

(51) Int. Cl.
*C07C 15/085* (2006.01)
*C07C 2/86* (2006.01)
*C07C 37/08* (2006.01)
(52) U.S. Cl. .................. 585/447; 585/446; 568/798
(58) Field of Classification Search .............. 585/447
See application file for complete search history.

(56) References Cited

U.S. PATENT DOCUMENTS

| | | | |
|---|---|---|---|
| 5,017,729 A | 5/1991 | Fukuhara et al. | |
| 6,372,927 B2 | 4/2002 | Tatsumi et al. | |
| 6,841,704 B2 * | 1/2005 | Sakuth et al. | 568/798 |
| 8,273,932 B2 * | 9/2012 | Senoo et al. | 585/469 |

FOREIGN PATENT DOCUMENTS

| | | |
|---|---|---|
| CN | 101111461 A | 1/2008 |
| JP | 02-174737 | 6/1990 |
| JP | 02-231442 | 9/1990 |
| JP | 11-35497 | 2/1999 |
| JP | 11-116523 | 4/1999 |
| JP | 11-347574 | 12/1999 |
| JP | 2003-523985 | 8/2003 |
| JP | 2005-314424 | 11/2005 |
| WO | 96-04225 | 2/1996 |
| WO | 03/053892 | 7/2003 |
| WO | 2006/060158 | 6/2006 |

OTHER PUBLICATIONS

International Search Report dated Aug. 31, 2009.
Ipatieff, V., Teodorovitch, V.P., Levine, I.M., Solubility of Hydrogen and Natural Gas in Oil at High Operating Temperature and Pressure., The Oil and Gas Journal, 32, pp. 14, 30, and 31, Oct. 5, 1933.
Shokubai Kouza (Catalyst Courses) vol. 6, (Engineering Part 2), Shokubai Hannou Souchi to Sono Sekkei (Catalyst reaction apparatus and its design), Catalysts Society of Japan, Kodansha Ltd., Dec. 1985, first impression, p. 182.
Sokolov V., J. Appl. Chem. USSR, 50(6), 1347-1349, (1977).
Thompson W. H., J. Chem. Eng. Data, 9(4), 516-520, (1964).
Englin B. A., Khim. Tekhnol. Topl. Masel, 10(9), 42-46, (1965).
Search Report and Written Opinion prepared by Hungarian Patent Office issued in connection with the corresponding Singapore application (No. 201008886-2) dated Feb. 3, 2012.
Industrial & Engineering Chemistry Research, vol. 45, No. 10, pp. 3481-3487 (2006).
Kagaku Kougaku Binran (Chemical Engineering Handbook), revised 6th edition, edited by The Society for Chemical Engineers, Japan, pp. 79-80 (1999).
Chinese Office Action issued in connection with the corresponding application (No. 200980121395.8) dated Jan. 7, 2013.

* cited by examiner

*Primary Examiner* — Brian J Davis
(74) *Attorney, Agent, or Firm* — Rankin, Hill & Clark LLP

(57) ABSTRACT

The invention provides an efficient process for producing alkylated aromatic compounds such as cumene in a compact reactor. The invention also provides a process for producing phenol which includes a step of producing cumene by the above process. The process for producing alkylated aromatic compounds of the invention includes feeding raw materials including an aromatic compound and an alcohol in a gas-liquid downward concurrent flow mode to a fixed-bed reactor packed with a solid acid catalyst thereby to produce an alkylated aromatic compound, wherein the raw materials are fed to the reactor in a stream of a gas, and the reaction gas flow rate defined by the equation below is not less than 0.05 at an entrance of a solid acid catalyst layer:

$$\rho g \cdot ug \cdot [\rho air \cdot \rho water/(\rho g \cdot \rho l)]^{1/2} (kgm^{-2}s^{-1}).$$

14 Claims, 1 Drawing Sheet

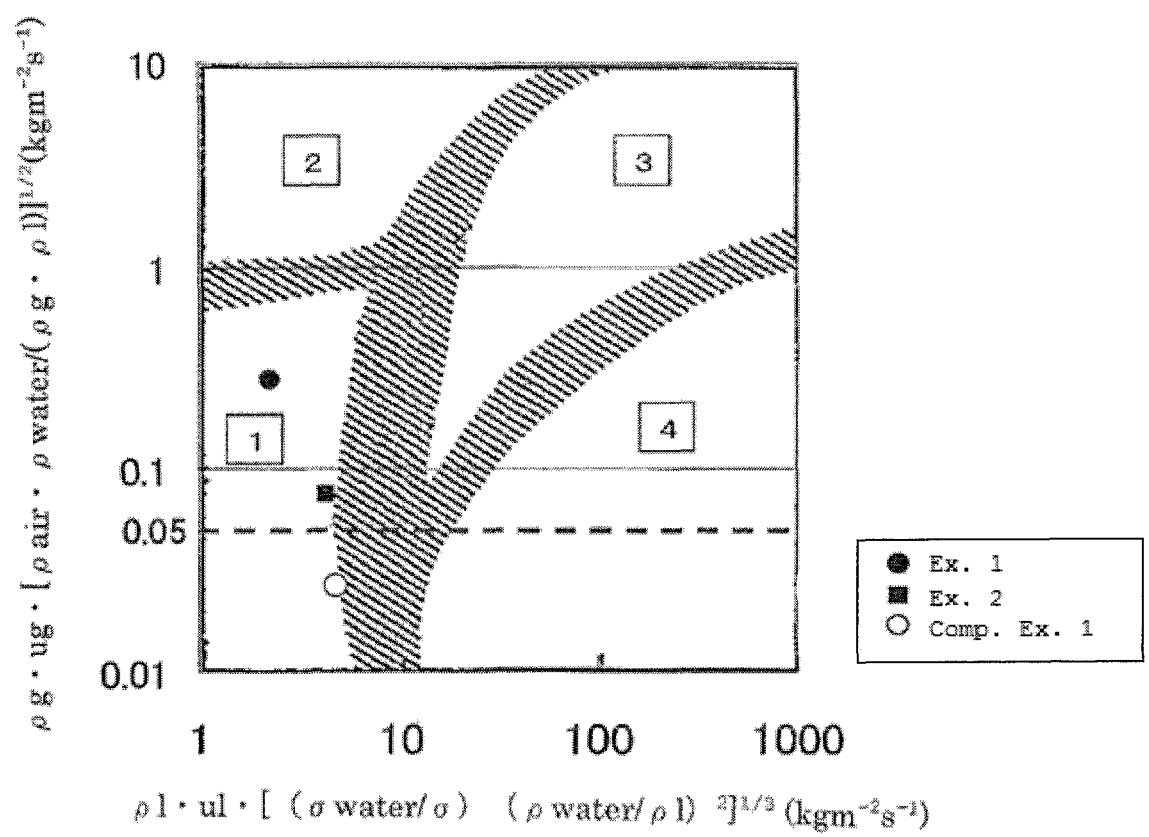

PROCESS FOR PRODUCING ALKYLATED AROMATIC COMPOUNDS AND PROCESS FOR PRODUCING PHENOL

TECHNICAL FIELD

The present invention relates to processes for producing alkylated aromatic compounds and processes for producing phenol.

BACKGROUND ART

The cumene process in which phenol is produced from cumene as a starting material is known. The cumene process gives by-product acetone in an equimolar amount to the phenol produced. The by-product acetone has a wide range of applications as solvent or organic synthesis material. However, depending on market trends which differ at different times, the acetone by-produced is in excess or the market conditions thereof are adverse, thereby lowering economic efficiency of phenol. The cumene is usually produced by alkylating benzene with propylene. The propylene is manufactured by thermal cracking of naphtha. Depending on the demand balance between propylene and ethylene which is another product by the naphtha cracking, propylene shortage is often brought about which is a bottleneck in the production for cumene.

To avoid the bottleneck, Patent Literature 1 discloses a process in which acetone by-produced in the phenol production is hydrogenated to isopropanol, the isopropanol is dehydrated to propylene, and the propylene is recycled as a material in the cumene production or the like. However, the hydrogenation and the dehydration add two steps.

To reduce steps, Patent Literatures 2 to 4 disclose methods in which isopropanol from the hydrogenation of acetone is directly used as an alkylating agent without dehydration and is reacted with benzene to give cumene. Patent Literature 4 discloses that the process involves a trickle-bed reactor, but is silent on the flow rate of gas.

CITATION LIST

Patent Literature
 Patent Literature 1: JP-A-H02-174737
 Patent Literature 2: JP-A-H02-231442
 Patent Literature 3: JP-A-H11-35497
 Patent Literature 4: JP-A-2003-523985

SUMMARY OF INVENTION

Technical Problem

When an alcohol is used as an alkylating agent in the production of alkylated aromatic compounds, the reaction forms an equivalent amount of water to the alkylating agent that has reacted. As known in the art, the water poisons solid acid catalysts which are the alkylation catalysts. It is therefore expected that the catalytic activity and the catalyst life are lowered compared to conventional processes using olefins as the alkylating agents. Accordingly, larger amounts of catalysts are required, and the throughput of the aromatic compound (benzene) and alcohol (isopropanol) per catalyst weight, in detail the liquid weight hourly space velocity (WHSV), is lowered. To cope with these problems, the reactor size should be excessively large, increasing equipment costs.

Such disadvantages should be solved in the industrial production of alkylated aromatic compounds using alcohols as alkylating agents.

It is an object of the present invention to provide an efficient process for producing alkylated aromatic compounds such as cumene by reacting raw materials including an aromatic compound and an alcohol in the presence of a solid acid catalyst in a compact reactor. It is another object of the invention to provide a process for producing phenol which includes a step of producing cumene by the above alkylation process.

Solution to Problem

The present inventors studied diligently to solve the aforementioned problems. They have then found that aromatic compounds may be alkylated with an alkylating agent alcohol such as isopropanol in a fixed-bed reactor packed with a solid acid catalyst as an alkylation catalyst with very high conversion of the alkylating agent and very high cumene selectivity by passing gas through the reactor.

In detail, the present invention is concerned with processes for producing alkylated aromatic compounds and processes for producing phenol as described in (1) to (7) below.

(1) A process for producing alkylated aromatic compounds comprising feeding raw materials including an aromatic compound and an alcohol in a gas-liquid downward concurrent flow mode to a fixed-bed reactor packed with a solid acid catalyst thereby to produce an alkylated aromatic compound, wherein the raw materials are fed to the reactor in a stream of gas, and the reaction gas flow rate defined by Equation (1) below is not less than 0.05 at an entrance of a solid acid catalyst layer:

$$\rho g \cdot ug \cdot [\rho air \cdot \rho water/(\rho g \cdot \rho l)]^{1/2} (\text{kgm}^{-2}\text{s}^{-1}) \qquad (1)$$

wherein $\rho g$ is the density of the reaction gas, $\rho l$ is the density of the reaction liquid, $\rho air$ is the gas density of air, $\rho water$ is the gas density of water, and $ug$ is the superficial velocity of the reaction gas.

(2) The process for producing alkylated aromatic compounds as described in (1), wherein the flow state in the reactor is in a trickle-bed zone.

(3) The process for producing alkylated aromatic compounds as described in (1) or (2), wherein the gas is at least one gas selected from the group consisting of nitrogen, hydrogen and rare gases.

(4) The process for producing alkylated aromatic compounds as described in any one of (1) to (3), wherein the solid acid catalyst is zeolite.

(5) The process for producing alkylated aromatic compounds as described in (4), wherein the zeolite has a ten to twelve-membered ring structure.

(6) The process for producing alkylated aromatic compounds as described in any one of (1) to (5), wherein the aromatic compound is benzene and the alcohol is isopropanol.

(7) A process for producing phenol, comprising the step (a) to the step (e) described below wherein the step (d) is performed according to the process for producing alkylated aromatic compounds described in (6);

step (a): a step of oxidizing cumene into cumene hydroperoxide;

step (b): a step of acid decomposing the cumene hydroperoxide to obtain phenol and acetone;

step (c): a step of hydrogenating the acetone from the step (b) to isopropanol;

step (d): a step of reacting the isopropanol from the step (c) with benzene to synthesize cumene; and step (e): a step of circulating the cumene from the step (d) to the step (a).

Advantageous Effects of Invention

According to the processes for producing alkylated aromatic compounds of the present invention, an alcohol such as isopropanol and an aromatic compound such as benzene (raw materials) are fed to a reactor in a stream of a gas, and thereby alkylated aromatic compounds such as cumene can be produced in a higher yield than achieved heretofore with industrial and practical advantages.

The processes for producing phenol according to the invention have adopted the above process of producing alkylated aromatic compounds, and thereby acetone that is by-produced in the phenol production can be reused.

BRIEF DESCRIPTION OF DRAWING

FIG. 1 is a plot diagram in which flow states in Examples and Comparative Example are plotted in a diagram showing flow zones in gas-liquid downward concurrent packed layers that is described in "Shokubai Kouza (Catalyst Courses) Vol. 6, (Engineering Part 2), Shokubai Hannou Souchi to Sono Sekkei (Catalyst reaction apparatus and its design)", Catalysts Society of Japan, Kodansha Ltd., December 1985, first impression, p. 182.

DESCRIPTION OF EMBODIMENTS

In a process for producing alkylated aromatic compounds according to the invention, raw materials including an aromatic compound and an alcohol are fed in a gas-liquid downward concurrent flow mode to a fixed-bed reactor packed with a solid acid catalyst thereby to produce an alkylated aromatic compound. The raw materials are fed to the reactor under a stream of a gas. The reaction gas flow rate defined by Equation (1) below is not less than 0.05 at an entrance of a solid acid catalyst layer:

$$\rho g \cdot ug \cdot [\rho air \cdot \rho water/(\rho g \cdot \rho l)]^{1/2} (kgm^{-2}s^{-1}) \quad (1)$$

wherein $\rho g$ is the density of the reaction gas, $\rho l$ is the density of the reaction liquid, $\rho air$ is the gas density of air, $\rho water$ is the gas density of water, and $ug$ is the superficial velocity of the reaction gas.

The solid acid catalyst layer is a catalyst layer formed by loading the solid acid catalyst in the fixed-bed reactor.

The reaction in the process for producing alkylated aromatic compounds according to the invention is the alkylation of an aromatic compound with an alcohol in the presence of a solid acid catalyst, and is a liquid solid two phase reaction. According to the finding by the present inventors, the reaction results of the alkylation are drastically improved by feeding the raw materials to the reactor under a stream of a gas.

Flow zones in gas-liquid downward concurrent flow mode are shown in FIG. 1. The flow zone diagram is based on data obtained with an air-water system. Flow zones with other systems may be prepared in consideration of correction terms based on differing physical properties ("Shokubai Kouza (Catalyst Courses) Vol. 6, (Engineering Part 2), Shokubai Hannou Souchi to Sono Sekkei (Catalyst reaction apparatus and its design)", Catalysts Society of Japan, Kodansha Ltd., December 1985, first impression, p. 182). The shaded parts in FIG. 1 indicate ranges where boundaries exist. The x-axis and y-axis in the diagram are defined as follows:

x-axis: $\rho l \cdot ul \cdot [(\phi water/\phi)(\rho water/\rho l)^{1/2}](kgm^{-2}s^{-1})$
y-axis: $\rho g \cdot ug \cdot [\rho air \cdot \rho water/(\rho g \cdot \rho l)]^{1/2}(kgm^{-2}s^{-1})$ Here, $\rho l$, $\rho g$, $\rho air$ and $\rho water$ are the density of the reaction liquid, the density of the reaction gas, the gas density of air and the gas density of water, respectively, $\phi$ and $\phi water$ respectively indicate the surface tension of the reaction liquid and the surface tension of water, and $ul$ and $ug$ are the superficial velocity of the reaction liquid and that of the reaction gas, respectively.

In the invention, the reaction gas refers to a gas phase component in the reactor. That is, the reaction gas includes all components existing in the form of gas, in detail the gas used to feed the raw materials in a gas-liquid downward concurrent flow mode, evaporated aromatic compound and alcohol, and evaporated alkylated aromatic compound and water. In the invention, the reaction liquid refers to a liquid phase component in the reactor. That is, the reaction liquid includes all components existing in the form of liquid, in detail aromatic compound and alcohol fed as raw materials, gas dissolved in the liquid phase, and alkylated aromatic compound and water.

In the invention, the flow state in the reactor is preferably in a trickle-bed zone (perfusate flow). In the trickle-bed zone, the liquid trickles over the outer surface of the catalyst and part thereof is attached to narrow pores in the catalyst. In either case, the liquid is scattered as individual masses forming a dispersed phase. Meanwhile, the gas surrounds the catalyst and the liquid, forming a continuous phase.

When the flow state in the reactor is in a trickle-bed zone, the concentration distribution in the system is uniform and mild operation is possible, the facility does not have to be high-pressure resistant, the physical load on the catalyst is lowered, and catalyst damage is prevented as described in JP-A-H11-116523.

In the invention, the reaction gas flow rate defined by Equation (1) below is not less than 0.05 at an entrance of the solid acid catalyst layer.

$$\rho g \cdot ug \cdot [\rho air \cdot \rho water/(\rho g \cdot \rho l)]^{1/2} (kgm^{-2}s^{-1}) \quad (1)$$

wherein $\rho g$ is the density of the reaction gas, $\rho l$ is the density of the reaction liquid, $\rho air$ is the gas density of air, $\rho water$ is the gas density of water, and $ug$ is the superficial velocity of the reaction gas.

Equation (1) above corresponds to the y-axis in the flow zone diagram in FIG. 1. When the reaction gas flow rate defined by Equation (1) is 0.05 or above, high cumene selectivity is achieved. The reaction gas flow rate is more preferably in the range of 0.08 to 0.6.

In FIG. 1, the x-axis indicates the flow rate of the reaction liquid (the liquid phase component in the reactor), represented by Equation (2) below. The reaction liquid flow rate represented by Equation (2) has been found less influential to the efficiency and results of the production of alkylated aromatic compounds by the processes according to the present invention, compared to the reaction gas flow rate expressed by Equation (1).

$$\rho l \cdot ul \cdot [(\phi water/\phi)/(\rho water/\rho l)^2]^{1/3} (kgm^{-2}s^{-1}) \quad (2)$$

wherein $\rho l$ is the density of the reaction liquid, $\rho water$ is the gas density of water, $\phi$ is the surface tension of the reaction liquid, $\phi water$ is the surface tension of water, and $ul$ is the superficial velocity of the reaction liquid.

As described hereinabove, it is preferable in the processes for producing alkylated aromatic compounds that the flow state in the reactor is in a trickle-bed zone. The flow rate of the reaction liquid does not adversely affect the processes of the invention as long as the flow state is in a trickle-bed zone.

Examples of the aromatic compounds used in the processes for producing alkylated aromatic compounds include benzene and naphthalene, with benzene being preferred. Examples of the alcohols include isopropanol and 2-butanol, with isopropanol being preferred.

That is, in a preferred embodiment of the processes for producing alkylated aromatic compounds of the invention, the aromatic compound is benzene and the alcohol is isopropanol, and the alkylated aromatic compound obtained in this case is cumene.

In the invention, at least one gas selected from the group consisting of nitrogen, hydrogen and rare gases is used.

The solid acid catalysts used in the invention are catalysts that function as acids. Examples of the solid acid catalysts include usual solid acids such as zeolite, silica alumina, alumina, sulfate-promoted zirconia and $WO_3$-promoted zirconia.

In particular, the zeolites that are inorganic crystalline porous compounds composed of silicon and aluminum are suitable solid acid catalysts from the viewpoints of heat resistance and selectivity for the target alkylated aromatic compounds (such as cumene).

For the production of cumene as the alkylated aromatic compound, a zeolite is preferably used which has a ten to twelve-membered ring structure having a pore similar in size to the molecular diameter of cumene.

Examples of the zeolites having a twelve-membered ring structure include Y-type zeolite, USY-type zeolite, mordenite type zeolite, dealuminated mordenite type zeolite, β-zeolite, MCM-22-type zeolite and MCM-56-type zeolite. In particular, β-zeolite, MCM-22-type zeolite and MCM-56-type zeolite have suitable structures.

In the zeolites, the composition ratio between silicon and aluminum may be suitably in the range of 2/1 to 200/1, and in view of activity and heat stability, preferably in the range of 5/1 to 100/1. Further, isomorphously substituted zeolites may be used in which aluminum atoms in the zeolite skeleton are substituted with other metal such as Ga, Ti, Fe, Mn or B.

The shape of the solid acid catalysts is not particularly limited, and the solid acid catalysts may be in the form of sphere, cylindrical column, extrudate or crushed pieces. The size of the particles of the solid acid catalysts may be selected in the range of 0.01 mm to 100 mm depending on the size of a reactor.

To achieve high productivity, the supply rate for the raw materials in the invention, in detail the liquid weight hourly space velocity (WHSV) relative to the catalyst weight is preferably not more than 50, more preferably not more than 20, and still more preferably not more than 10. The liquid weight hourly space velocity (WHSV) is usually not less than 1.

The above supply rate ensures that cumene is produced in a high yield.

Theoretically, the aromatic compound may be used at least in an equimolar amount relative to the alcohol. From the viewpoints of separation and recovery, the aromatic compound may be preferably used in an equimolar to ten-fold molar amount, and more preferably in an equimolar to five-fold molar amount relative to the alcohol.

From the viewpoints of separation and recovery, the gas in the invention may be preferably used in an equimolar to twenty-fold molar amount, and more preferably in an equimolar to ten-fold molar amount relative to the alcohol.

In the processes for producing alkylated aromatic compounds, the raw materials are fed to a fixed bed reactor in a gas-liquid downward concurrent flow mode. The reaction temperature in the reactor is in the range of 100 to 300° C., and preferably 120 to 250° C. The reaction pressure is in the range of 0.5 to 10 MPaG, and preferably 2 to 5 MPaG.

A process for producing phenol according to the present invention includes the step (a) to the step (e) described below wherein the step (d) is performed according to the process for producing alkylated aromatic compounds described hereinabove. In the process for producing alkylated aromatic compounds which is performed as the step (d) in the phenol production process, the aromatic compound is benzene and the alcohol is isopropanol.

Step (a): a step of oxidizing cumene into cumene hydroperoxide;

Step (b): a step of acid decomposing the cumene hydroperoxide to obtain phenol and acetone;

Step (c): a step of hydrogenating the acetone from the step (b) to isopropanol;

Step (d): a step of reacting the isopropanol from the step (c) with benzene to synthesize cumene; and Step (e): a step of circulating the cumene from the step (d) to the step (a).

In the process for producing phenol, phenol is formed from cumene in the steps (a) and (b), the by-product acetone is hydrogenated in the step (c) to isopropanol, the isopropanol is reacted in the step (d) to form cumene, and the cumene formed in the step (d) is recycled in the step (e) back to the step (a). Accordingly, it is theoretically not necessary that acetone should be fed from the outside of the reaction system, achieving cost advantages. In practical plants, it is difficult to recover 100% acetone and therefore at least an amount of acetone corresponding the decrease is newly fed to the reaction system.

Various modifications and improvements may be made to the processes for producing, phenol according to the invention.

EXAMPLES

The present invention will be described by presenting examples but the invention is not limited to such examples as long as within the scope of the invention.

Example 1

A catalyst test was carried out in which cumene was produced from isopropanol and benzene as raw materials.

β-zeolite catalyst (pellets 1.5 mm in diameter, manufactured by TOSOH CORPORATION) weighing 2435 g was loaded in a stainless steel vertical reaction tube 38.4 mm in inner diameter and 4800 mm in length. After the loading, isopropanol was supplied from the top of the reactor at 24 L/h and the catalyst was washed for 1 hour.

While the reactor pressure was maintained at 3 MPaG and the preheating temperature at 175° C., benzene: 8.1 L/h, isopropanol: 0.65 L/h and hydrogen: 1900 NL/h were supplied from the top of the reactor to perform reaction. The liquid weight hourly space velocity (WHSV) under these conditions was 3.0. A mixture of the reaction liquid and gas that was discharged from the reactor bottom was separated in a gas-liquid separation tank, and the oil phase and the aqueous phase were separated in an oil-water separation tank. When the reaction had been continuously carried out for 12 hours, the reaction liquid and the waste gas were each analyzed by gas chromatography. The gas chromatography showed that the isopropanol conversion was 100% and the cumene selectivity was high at 92.8%.

Separately, a flow zone under the above conditions was studied. The reaction gas flow rate at the entrance of the solid acid catalyst layer (the alkylation catalyst layer) was calculated using the PSRK equation (Kagaku Kougaku Binran (Chemical Engineering Handbook), revised 6th edition, edited by The Society for Chemical Engineers, Japan.) as an estimation equation which had been corrected by regressing literature data including solubility data of hydrogen in benzene and cumene (Ipatieff V., Oil Gas J. 32, 14-15, (1993) and Sokolov V., J. Appl. Chem. USSR, 50(6), 1347-1349, (1977)), solubility data of benzene and cumene in water (Thompson W. H., J. Chem. Eng. Data, 9(4), 516-520, (1964) and Englin B. A., Khim. Tekhnol. Topl. Masel, 10(9), 42-46, (1965)) and benzene/water azeotropic data (Burd S. D., Proc. Am. Petrol. Inst. Ref. Div., 48, 464-476, (1968)).

Properties were estimated by inputting the above estimation equation and reaction conditions in Examples in a stationary process simulator (manufactured by Aspen Tech Japan Co., Ltd.). The results are set forth in Table 1.

In Example 1, the flow state was in a trickle-bed zone and the reaction gas flow rate was 0.280.

x-axis: $\rho l \cdot ul \cdot [(\phi water \cdot /\phi)(\rho water/\rho l)^2]^{1/3}$ (kgm$^{-2}$s$^{-1}$)= 2.263 y-axis: $\rho g \cdot ug \cdot [\rho air \cdot \rho water/(\rho g \cdot \rho l)]^{1/2}$ (kgm$^{-2}$s$^{-1}$)=0.280

Example 2

A catalyst test was carried out with the same experimental apparatus and under the same reaction conditions as in Example 1, except that the hydrogen was fed at 500 NL/h. The isopropanol conversion was 100% and the cumene selectivity was high at 86.9%.

In Example 2, the flow state was in a trickle-bed zone and the reaction gas flow rate was 0.075.

x-axis: $\rho l \cdot ul \cdot [(\phi water/\phi)(\rho water/\rho l)^2]^{1/3}$ (kgm$^{-2}_s{}^{-1}$)= 4.269 y-axis: $\rho g \cdot ug \cdot [\rho air \cdot \rho water/(\rho g \cdot \rho l)]^{1/2}$ (kgm$^{-2}$s$^{-1}$)=0.075

Comparative Example 1

A catalyst test was carried out with the same experimental apparatus and under the same reaction conditions as in Example 1, except that the hydrogen was fed at 190 NL/h. The isopropanol conversion was 50.5% and the cumene selectivity was low at 42.6%. Further, large amounts of by-product propane and propylene were produced.

In Comparative Example 1, the flow state was in a trickle-bed zone, but the reaction gas flow rate was 0.026.

x-axis: $\rho l \cdot ul \cdot [(\phi water/\phi)(\rho water/\rho l)^2]^{1/3}$ (kgm$^{-2}_s{}^{-1}$)= 4.771 y-axis: $\rho g \cdot ug \cdot [\rho air \cdot \rho water/(\rho g \cdot \rho l)]^{1/2}$ (kgm$^{-2}$s$^{-1}$)=0.026

The invention claimed is:

1. A process for producing alkylated aromatic compounds comprising feeding raw materials including an aromatic compound and an alcohol in a gas-liquid downward concurrent flow mode to a fixed-bed reactor packed with a solid acid catalyst thereby to produce an alkylated aromatic compound, wherein
   the raw materials are fed to the reactor in a stream of a gas, and
   the reaction gas flow rate defined by Equation (1) below is not less than 0.05 at an entrance of a solid acid catalyst layer:

$$\rho g \cdot ug \cdot [\rho air \cdot \rho water/(\rho g \cdot \rho l)]^{1/2} (kgm^{-2}s^{-1}) \qquad (1)$$

wherein $\rho g$ is the density of the reaction gas, $\rho l$ is the density of the reaction liquid, $\rho air$ is the gas density of air, $\rho water$ is the gas density of water, and ug is the superficial velocity of the reaction gas.

2. The process for producing alkylated aromatic compounds according to claim 1, wherein the flow state in the reactor is in a trickle-bed zone.

3. The process for producing alkylated aromatic compounds according to claim 1, wherein the gas is at least one gas selected from the group consisting of nitrogen, hydrogen and rare gases.

4. The process for producing alkylated aromatic compounds according to claim 1, wherein the solid acid catalyst is zeolite.

5. The process for producing alkylated aromatic compounds according to claim 4, wherein the zeolite has a ten to twelve-membered ring structure.

6. The process for producing alkylated aromatic compounds according to claim 1, wherein the aromatic compound is benzene and the alcohol is isopropanol.

7. A process for producing phenol, comprising the step (a) to the step (e) described below wherein the step (d) is performed according to the process for producing alkylated aromatic compounds described in claim 6;
   step (a): a step of oxidizing cumene into cumene hydroperoxide;
   step (b): a step of acid decomposing the cumene hydroperoxide to obtain phenol and acetone;

TABLE 1

| Properties at entrance of zeolite layer | | Ex. 1 | | Ex. 2 | | Comp. Ex. 1 | |
|---|---|---|---|---|---|---|---|
| | | Liquid phase component | Gas phase component | Liquid phase component | Gas phase component | Liquid phase component | Gas phase component |
| Surface tension | dyne/cm | 9.770 | — | 9.716 | — | 9.693 | — |
| Viscosity | cP | 0.143 | 0.017 | 0.143 | 0.016 | 0.142 | 0.016 |
| Density | kg/m$^3$ | 615.247 | 27.196 | 607.994 | 28.817 | 604.981 | 29.430 |
| Flow rate | kg/h | 3.501 | 4.358 | 6.540 | 1.192 | 7.280 | 0.424 |
| Superficial velocity | kg/m$^2 \cdot$s | 0.840 | 1.046 | 1.569 | 0.286 | 1.747 | 0.102 |
| x-axis (Eq. 2) | kg/m$^2 \cdot$s | 2.263 | | 4.269 | | 4.771 | |
| y-axis (Eq. 1) | kg/m$^2 \cdot$s | 0.280 | | 0.075 | | 0.026 | |

REFERENCE SIGNS LIST

1 . . . perfusate flow
2 . . . mist flow
3 . . . pulsating flow
4 . . . bubble flow step (c): a step of hydrogenating the acetone from the step (b) to isopropanol;
step (d): a step of reacting the isopropanol from the step (c) with benzene to synthesize cumene; and
step (e): a step of circulating the cumene from the step (d) to the step (a).

8. The process for producing alkylated aromatic compounds according to claim 2, wherein the gas is at least one gas selected from the group consisting of nitrogen, hydrogen and rare gases.

9. The process for producing alkylated aromatic compounds according to claim 2, wherein the solid acid catalyst is zeolite.

10. The process for producing alkylated aromatic compounds according to claim 3, wherein the solid acid catalyst is zeolite.

11. The process for producing alkylated aromatic compounds according to claim 2, wherein the aromatic compound is benzene and the alcohol is isopropanol.

12. The process for producing alkylated aromatic compounds according to claim 3, wherein the aromatic compound is benzene and the alcohol is isopropanol.

13. The process for producing alkylated aromatic compounds according to claim 4, wherein the aromatic compound is benzene and the alcohol is isopropanol.

14. The process for producing alkylated aromatic compounds according to claim 5, wherein the aromatic compound is benzene and the alcohol is isopropanol.

\* \* \* \* \*